(12) United States Patent
Moger (10) Patent No.: US 9,352,130 B2
(45) Date of Patent: May 31, 2016

(54) TORQUE DEVICE FOR A GUIDEWIRE

(71) Applicant: Adrian Moger, Fairview, TX (US)

(72) Inventor: Adrian Moger, Fairview, TX (US)

(73) Assignee: Adrian Moger, Fairview, TX (US)

( * ) Notice: Subject to any disclaimer, the term of this patent is extended or adjusted under 35 U.S.C. 154(b) by 74 days.

(21) Appl. No.: 14/214,447

(22) Filed: Mar. 14, 2014

(65) Prior Publication Data

US 2014/0276225 A1    Sep. 18, 2014

Related U.S. Application Data

(60) Provisional application No. 61/793,164, filed on Mar. 15, 2013.

(51) Int. Cl.
*A61B 5/00* (2006.01)
*A61M 25/00* (2006.01)
*A61M 25/09* (2006.01)

(52) U.S. Cl.
CPC ..... *A61M 25/09* (2013.01); *A61M 2025/09116* (2013.01)

(58) Field of Classification Search
CPC .................. A61M 25/09; A61M 25/09041
USPC .......................................... 600/585
See application file for complete search history.

(56) References Cited

U.S. PATENT DOCUMENTS

2003/0229297 A1* 12/2003 Christensen .... A61M 25/09041
600/585

* cited by examiner

*Primary Examiner* — Brian Szmal
(74) *Attorney, Agent, or Firm* — Maschoff Brennan (57) ABSTRACT

A torque device for attaching to and selectively gripping or securing and releasing a guidewire to permit rotational and longitudinal manipulation of the guidewire to steer and control the guidewire. In one embodiment the torque device comprises a nose portion, a neck portion, and a base portion with varying outer diameters for improved rotational control.

19 Claims, 12 Drawing Sheets

TORQUE DEVICE FOR A GUIDEWIRE

CROSS-REFERENCES AND RELATED APPLICATIONS

The present invention claims priority to provisional application No. 61/793,164, filed Mar. 15, 2013, entitled "TORQUE DEVICE FOR A GUIDEWIRE," which is herein incorporated by reference in its entirety.

BACKGROUND OF THE INVENTION

1. The Field of the Invention

The present invention relates to the field of medical devices, and more particularly to a medical guide wire torque device used for grasping and maneuvering guidewires during medical procedures.

2. The Relevant Technology

A number of medical procedures have been developed which include the introduction and manipulation of a medical guidewire into a patient. One example of such a procedure is angioplasty, where a guidewire is inserted via a vascular access needle into the femoral artery and subsequently manipulated at the proximal end of the guidewire by a torque so as to advance a distal end through a patient's arterial tree to a predetermined destination. Typically, a catheter, balloon or stent is then fed over the guidewire into the desired area to perform the desired medical procedure. Guidewires are also used in other medical applications in a similar manner.

The insertion and manipulation of guidewires is often a difficult and precise process. As the guidewire is negotiated through a patient's vessels or other tubular structures inside the body, the guidewire is controlled completely by manipulating the proximal end of the guidewire. In order to facilitate this manipulation, a torque device is fixed to the proximal end of the guidewire by threading or other means of attachment and the operator manipulates the guidewire by rotating or otherwise manipulating the torque device.

When using such torque devices, the operator relies on direct visualization of the wire using fluoroscopy or the like along with tactile feedback from the guidewire. In many instances, the tactile feedback supplied to the guidewire as the wire is guided as far as three or four feet within the vascular system of a patient is essential as an operator selects various passages, traverses areas where blocking or narrowing exist, and/or probes lesions.

One difficulty with the torque devices currently used in the art is that they focus on various means for reliably affixing the guidewire to the torque device, but fail to optimally or efficiently assist in providing an operator with the desired ability to manipulate the guidewire.

Figure 1:
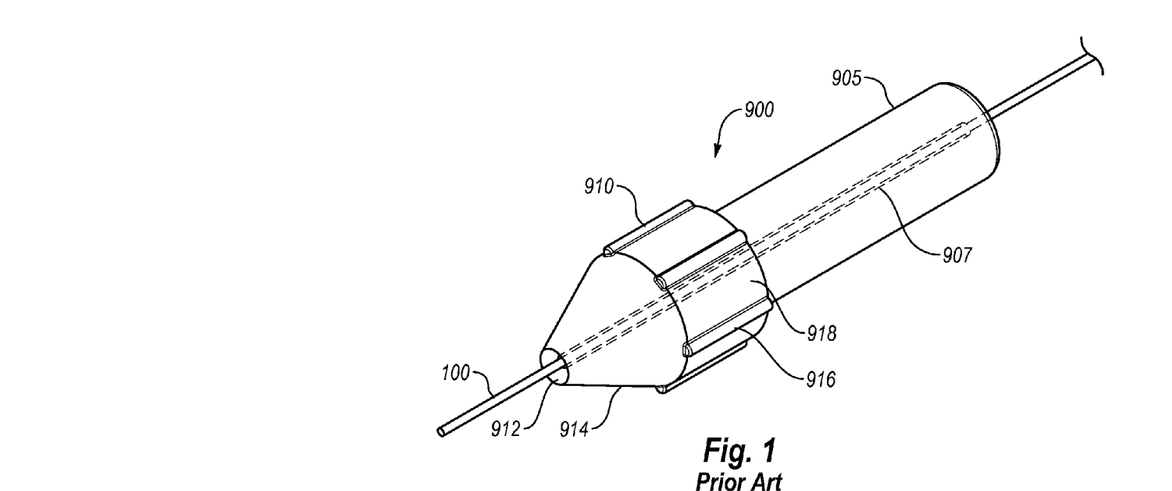
FIG. 1 illustrates a torque device currently known in the art.

Further, many known torque devices have only a simplistic cylindrical shape, such as the torque device 900 shown in FIG. 1, which has a cylindrically shaped body 905 which includes a lumen 907 with a sufficient diameter so as to allow a guidewire 100 to pass through. A cap 910 with an entry hole 912 connected to a lumen which extends through the cap (not shown), a tapered head 914, and a cylindrical portion 918 which affixes to the body 905 by means of corresponding threaded portions in the interior of the cylindrical portion 918 and the body 905. A series of ridges 916 are formed on the cylindrical portion 918 of the cap so as to assist in the threading process. The cylindrical portion 918 also houses a collet or other gripping means which includes a series of spindles which straddle the guidewire.

As the cap 910 and the body 905 are threaded together, the cap 910 and spindle are rotated with respect to each other, the threaded engagement of the spindle and cap causes the end of the spindles to advance along the bore within the cap 910, causing the spindles to close and tighten around the guidewire 100 so as to secure the guidewire 100. Once the cap 910 and the body 905 are threaded together and the guidewire 100 is secured, the operator manipulates the guidewire 100 by manipulating and rotating the cylindrical body 905 of the torque device 900. Reversing the direction for rotation between the cap 910 and the body 905 causes the spindles to release the grip on the guidewire 100.

This configuration contains various difficulties for an operator. For example, the torque device 900 requires two hands to properly secure the torque device 900 to the guidewire 100. Hence, as the guidewire 100 is positioned or traversed through a patient's body during a procedure, each time the guidewire 100 is advanced some distance, such as 2-8 cm, the operator is required to use both hands to loosen the cap 910 from the body 905 so that the cap 910 and the body 905 can be repositioned and subsequently reattached to the guidewire 100. This process is disadvantageous and time consuming because it requires the operator to relinquish control of the guidewire 100 as both hands are required to loosen and reattach the torque device 900 to the guidewire 100. This additional time results in additional time in performing the procedure, which in turn requires a patient to be sedated for longer periods of time, increases the amount of time required to perform the surgery, and reduces the ability to accurately control and place the guidewire.

Another disadvantage of the torque device 900 currently used in the art is that the cylindrical shape of the body 905 is uniform and offers only a limited amount of rotational control to an operator. Specifically, to rotate the torque device 900, and subsequently the guidewire, the operator "rolls" the body 905 back and forth between the operator's fingers and/or twisting the wrist. Such options realistically limit the ability to rotate the torque device greater than approximately 90 degrees.

Hence, in order to more accurately and effectively secure and manipulate a guidewire, improvements are needed in the design and operability of torque devices. The embodiments herein offer a torque device with a greater ability to secure and manipulate a guidewire. Although, the subject matter claimed herein is not limited to embodiments that solve any disadvantages or that operate only in environments such as those described above, rather, this background is only provided to illustrate one exemplary technology area where some embodiments described herein may be practiced.

BRIEF SUMMARY OF THE INVENTION

The present invention relates to the field of medical devices, and more particularly to a medical guide wire torque device used for grasping and maneuvering guidewires during medical procedures.

This Summary is provided to introduce a selection of concepts in a simplified form that are further described below in the Detailed Description. This Summary is not intended to identify key features or essential characteristics of the claimed subject matter, nor is it intended to be used as an aid in determining the scope of the claimed subject matter.

A first aspect of the invention is a medical torque device including a nose portion having a first outer circumference, a neck portion having a second outer circumference, the second outer circumference being smaller than the first outer circumference, and a base portion having a third outer circumference which is greater than the second outer circumference, wherein a distal end of the neck portion is connected to a proximal end of the nose portion and the base portion with an inner lumen which extends through the nose portion, neck portion, and base portion and through which a guidewire may pass.

A second aspect of the invention is a medical torque device including a first component and a base top portion. The first component includes a nose portion having a first outer circumference, a neck portion having a second outer circumference, the second outer circumference being smaller than the first outer circumference, a base bottom portion having a guidewire-locking groove where a guidewire positioned within the base bottom portion is exposed, and an inner lumen which extends through the nose portion, neck portion and base bottom portion which houses the guidewire. The base top portion includes a guidewire-locking ridge which is capable of applying a pinching force on the guidewire positioned within the guidewire-locking groove when the first component and the base bottom position are urged together. An urging means applies an urging force to urge the base top portion towards the base bottom portion of the first component.

A third aspect of the invention is a medical torque device including a first component, base top portion and an urging means. The first component includes a nose portion having a cylindrical shape having a first outer circumference, a neck portion having a cylindrical shape having an outer circumference with a cross-section with a polygonal shape having at least three sides and at least three vertices where the sides meet, a base bottom portion having a guidewire-locking groove where a guidewire positioned within the base bottom portion is exposed, and an inner lumen which extends through the nose portion, neck portion and base bottom portion which houses the guidewire. The base top portion includes a guidewire-locking ridge which is capable of applying a pinching force on the guidewire positioned within the guidewire-locking groove when the first component and the base bottom position are urged together. The urging means applies an urging force to urge the base top portion towards the base bottom portion of the first component, wherein the base top portion and the base bottom portion together form an assembled base portion which has a conical outer circumference wherein a distal end of an assembled base top portion and first portion at a region where the base bottom portion connects to the neck portion has a smaller circumference than a proximal end of the assembled base portion.

Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

Embodiments of the invention relate to a medical guidewire torque device which offers various advantages which are not currently available in torque devices which are currently used. Specifically, the embodiments described herein describe a torque device for attaching to and selectively gripping or securing and releasing a guidewire to permit rotational and longitudinal manipulation of the guidewire to steer the guidewire through a vessel, series of vessels, or other structures. As may be understood by one of skill in the art, a medical torque devices are also used to direct wires through other parts of the body, including, but not limited to, the kidneys, ureters, bladder, the liver and bile ducts, as well as body cavities such as the stomach, pleural space in the chest and the peritoneal space in the abdomen.

Embodiments described herein provide a medical torque device for attaching to and selectively gripping a guidewire. As may be understood by one of skill in the art, a variety of guidewires are known which vary in size from approximately an 0.010 inch diameter to a 0.038 inch diameter with varying guidewire styles, materials, and tip angles. The embodiments described herein are capable of being used with a variety of different guidewire configurations.

Figure 2:
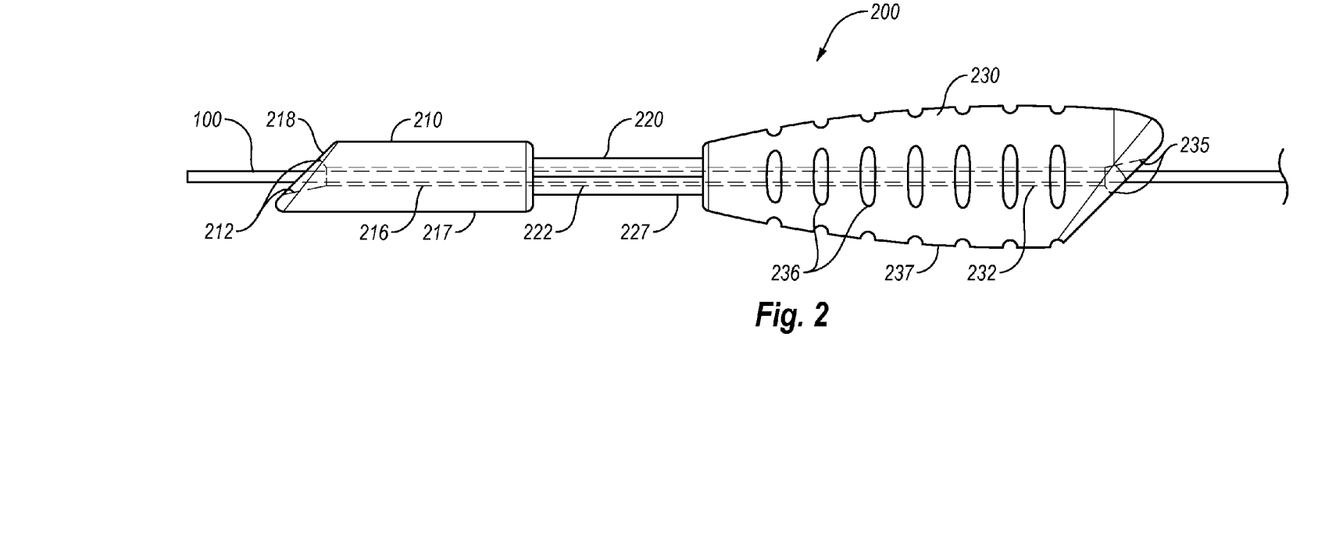
FIG. 2 is a side view of a torque device according to one embodiment of the invention.
Figure 3:
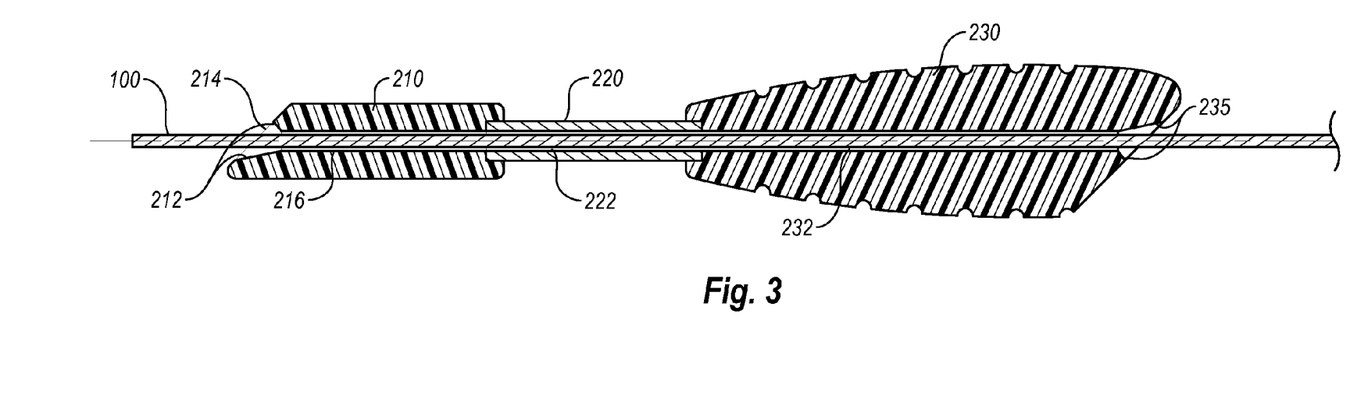
FIG. 3 is a cross-sectional view of the torque device shown in FIG. 2.

FIG. 2 is a side view of one example of a torque device 200 which is capable of performing various aspects of the invention and FIG. 3 is a cross-sectional view of the torque device 200 shown in FIG. 2. As shown in each of FIGS. 2 and 3, the torque device 200 of this embodiment includes three main segments, including a nose portion 210, a neck portion 220, and a base portion 230. As is described more fully below, the nose portion 210, the neck portion 220, and the base portion 230 are either manufactured and distributed as a single unit or manufactured as separate components which are subsequently connected together so as to form the assembled torque device 200.

The nose portion 210 illustrated herein has a cylindrical outer perimeter 217 and an inner lumen or bore 216 through which the guidewire 100 can pass. In one example, the bore 216 may have a diameter of 0.040 so as to accommodate a variety of different guidewire 100 sizes. The outer perimeter 217 of the nose portion 210 has a uniform shape and may be any diameter which assists in the loading of the guidewire 100 in the device. In some instances, the outer perimeter 217 may be formed of a material or shape which provides an improved gripping surface which would also assist in loading the guidewire 100.

In this example, the nose portion 210 has a length of approximately ¾ to ⅞ inches. As would be understood by those of skill in the art, however, the nose portion 210 may be formed in a variety of different shapes and lengths without departing from the meaning and scope of the invention.

The nose portion 210 also includes a beveled front or distal end 218 with an edge 214 formed so as to facilitate loading of the guidewire 100 and so as to provide a visual guide with respect to the rotational orientation or position of the guidewire 100. In one embodiment, the beveled front 218 has an approximately ⅛ inch differential from the top of the nose portion 210 to the bottom of the nose portion 210.

The bore 216 of the nose portion 210 also includes a conical front end recess 212 which has a larger diameter of the bore 216 at the beveled front 218 of the nose portion 210 and which tapers to meet the diameter of the bore 216 over a distance of ⅛ to 3/16 inches. The conical front end recess 212 also facilitates the loading and feeding of the guidewire 100.

The proximal portion of the nose portion 210 is connected to the neck portion 220. In this embodiment, the neck portion 220 has an inner lumen or bore 222 with a diameter which corresponds to the diameter of the bore 216 of the nose portion 210. The neck portion 220 has a hexagonal outer perimeter 227 with a diameter which is smaller than that of the nose portion 210 or the base portion 230 so as to facilitate quick and controlled rotation of the torque device 200. In the embodiment shown in FIGS. 2-3, the diameter of hexagonal outer perimeter 227 of the neck portion 220 is equivalent of a #3 or #4 Allen wrench tool.

As may be understood by one of skill in the art, the hexagonal outer perimeter 227 of the neck portion 220 could have a plurality of shapes or sizes, including a variety of geometric shapes, including cylindrical, triangular, trapezoidal, pentagonal, and the like.

One advantage of the neck portion 220 described herein is that it facilitates the rotation of the tip of the guidewire 100 by enabling a controlled rolling of the torque device 200 back and forth between an operator's fingers and/or by the twisting of the operator's wrist. Specifically, as compared to the torque devices currently known in the art, where rotation is limited by the diameter of the uniformly-shaped cylinder, the hexagonal outer perimeter 227 enables an operator to quickly spin or drill the torque device 200 and consequently the guidewire 100. This ability to spin or drill is useful in instances where the guidewire 100 is required to advance into a difficult branch or through an area of blockage.

Further, the hexagonal outer perimeter 227 also provides a distinct tactile advantage over the smooth and uniform cylindrical outer diameter of the configurations known in the art. Each facet of the hexagonal outer perimeter 227 correlates with precisely 60 degrees of rotation and the facets provide a secure gripping surface while the relatively small diameter of the hexagonal outer perimeter 227 enables the neck portion 220 to be easily rolled between an operator's fingers without the facets of the hexagonal outer perimeter 227 interfering with rotation.

Although in the embodiments shown in the figures shown herein the diameter of the hexagonal outer perimeter 227 of the neck portion 220 is smaller than the outer diameter of both the nose portion 210 and the base portion 230, as may be understood by one of skill in the art, the diameter of the hexagonal outer perimeter 227 may be smaller than only one or both of the nose portion 210 and the base portion 230. As described above, one advantage of having the neck portion 220 having a smaller outer diameter than the nose portion 210 and the base portion 230 is that it provides a differing range of rotation than that provided by rotating the nose portion 210 or the base portion 230.

The neck portion 220 is connected at the proximal end to the base portion 230. As shown in FIGS. 2-3, the base portion 230 has a modified teardrop shape so as to conform to the hand of an operator. The base portion 230 has an inner lumen or bore 232 with a diameter which allows the guidewire 100 to pass there through. In a preferred embodiment, the bore 232 has the same diameter as the bore 222 of the neck portion 220 and the bore 216 of the nose portion 210. As is shown in FIGS. 2-3, the base portion 230 also includes taper 235 at the distal portion of the bore 232.

In one configuration the base portion 230 has a length of approximately one inch with an outer perimeter 237 with a front diameter of approximately ¼ inch and a distal or rear diameter of ⅜ inches. As shown in FIG. 2, the outer perimeter 237 of the base portion 230 has a plurality of contours 236 formed thereon which facilitate the grip and feel of the base portion 230 and consequently the torque device 200.

One advantage of the base portion 230 is that the varied diameter allows fine continuous variable control of the guidewire 100 depending on the finger position of the operator along the tear drop shaped axis.

Although the base portion 230 is described as having a teardrop shape, the base portion 230 may also have a uniform cylindrical shape or any variety of other configurations without departing from the meaning and scope of the invention. As may also be understood by one of skill in the art, any combination or number of grooves or ridges or other texture may be applied to the surface of the base portion 230 so as to provide improved grip or feel. Further, the contours 236 may be altogether removed from the base portion 230.

As described briefly above, in one embodiment, the torque device 200 may be comprised of a single body which is comprised of a single manufactured body. In such a configuration, the entire device may measure to approximately 2½ to 2 and ¾ inches in length and made of a medical grade plastic which can be packaged in a sterile fashion for use in a sterile procedure. The torque device 200 may also be designed to be disposable, such that after a single use, the torque device 200 is disposed of or destroyed so that it is not necessary to clean or re-sterilize the torque device 200. In most medical settings, the torque device 200 will be designed for single use so as to ensure proper sterilization technique.

Figure 4:
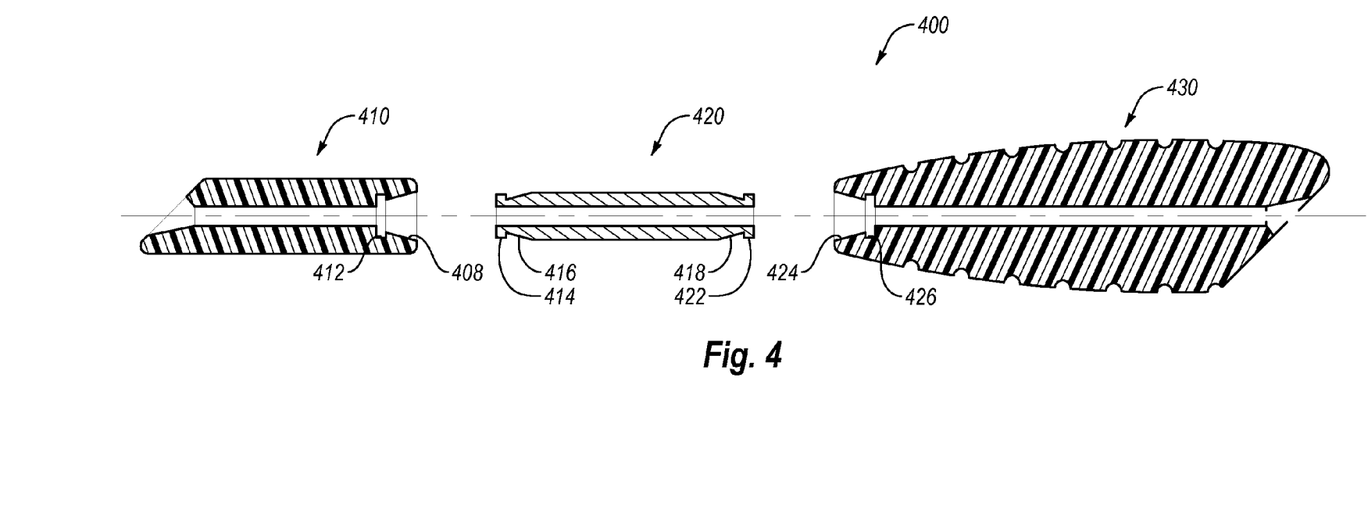
FIG. 4 is a cross-sectional view of the various interconnecting components of the torque device according to one embodiment of the invention.

Alternatively, as shown in FIG. 4, a nose portion 410, a neck portion 420, and a base portion 430 may be three separate components which may be separately manufactured and distributed. In such a configuration, a variety of different nose portions, neck portions, and base portions, each having differing outer diameters or shapes may be manufactured and distributed in a single sterilized package. Upon opening the package, the operator may select the nose portion 410, the neck portion 420, and the base portion 430 most suited for the operation on hand. The selected nose portion 410, neck portion 420 and base portion 430 may then be connected together quickly and securely at the onset of the operation.

In order to facilitate the connection between the different portions, the nose portion 410 includes a connection bevel 408 and a neck receiving portion 412 adapted to receive a distal neck connection portion 414 of the neck portion 420. The neck portion 420 also includes a distal bevel portion 416. The proximal portion of the neck portion 420 also includes a proximal neck connection portion 422 and a proximal bevel portion 418 which is adapted to be received by a bevel 424 and a neck receiving portion 426 of the base portion 430. The nose portion 410, the neck portion 420, and the base portion 430 shown in FIG. 4 are configured to be press-fitted together so as to form a connected torque device 400.

Figure 5:
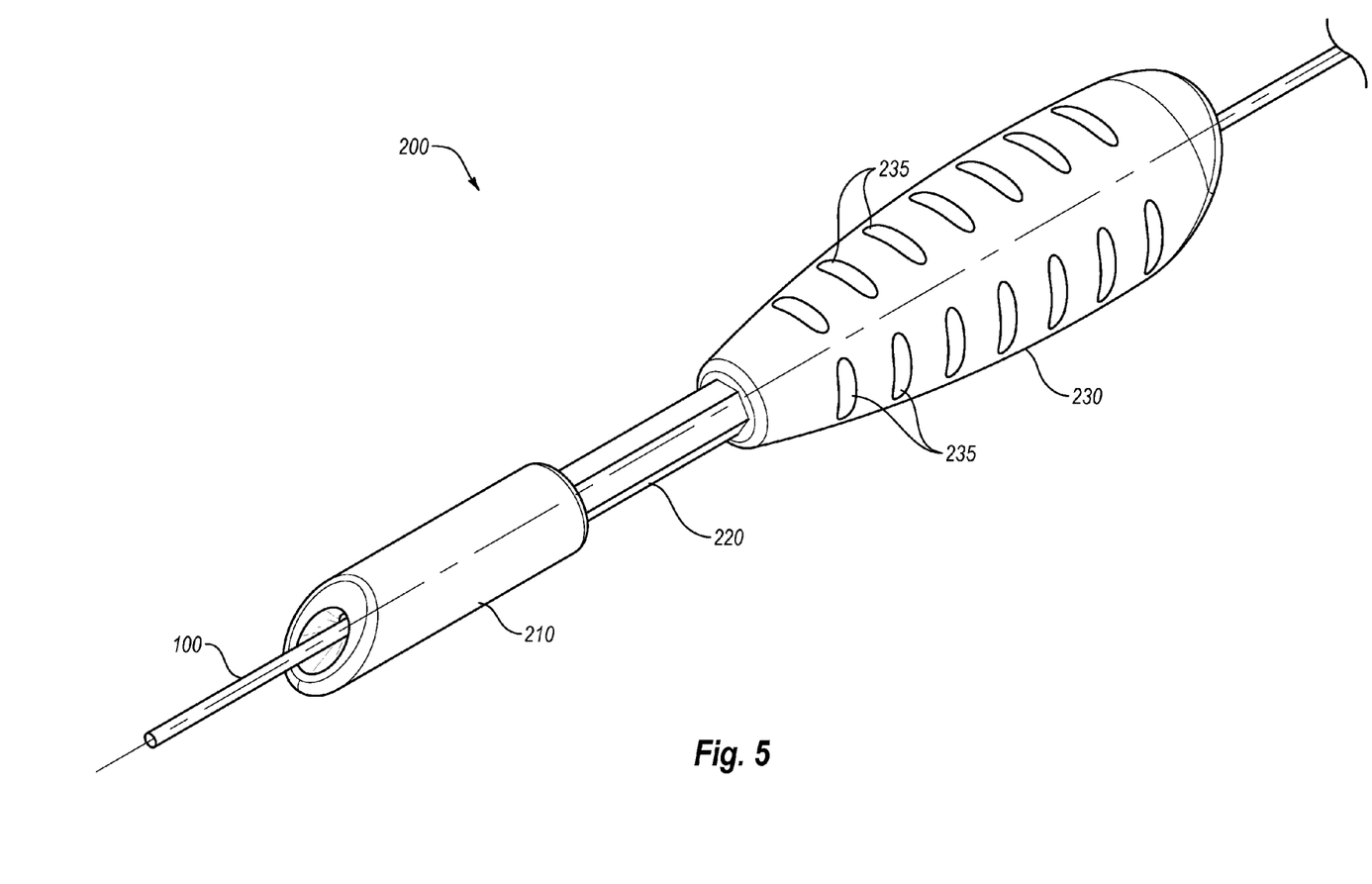
FIG. 5 is an isometric view of the torque device according to the embodiment shown in FIG. 2.

FIG. 5 is an isometric view of the torque device 200 formed as a single molded device 200. After assembly, the connected torque device 400 of FIG. 4 would have a similar appearance.

While FIG. 4 illustrates one means of connecting three separate portions, a variety of different connections may be used, including threaded connections, pin connections, or other connection means currently known or used in the art. Further, although FIGS. 2-5 show the nose portion 210, the neck portion 220, and the base portion 230 as each comprising a single molded component, as described below with respect to the base portion 230, each of the nose portion 210, the neck portion 220, and the base portion 230 may be comprised of two or more separate components which are connected together to form an assembled nose portion, neck portion, and/or base portion.

Further, although in the embodiments described in FIGS. 2-5 there is no specific means of locking or fixing the guidewire 100 to the torque device 200, a variety of different fixing means known in the art may be used in association with the shape and structure of the torque device 200 shown in FIGS. 2-5. For example, a collet locking mechanism, a pressurizing lever, clamping body, retaining ring, or the like may be used in either the nose portion 210, the neck portion 220, or the base portion 230 so as to secure the guidewire within the inner bores of the torque device 200.

Regardless of the means for fixing and securing the guidewire 100 within the torque device 200, the shape of the torque device 200 has distinct advantages. First, the nose portion 210 approximates the size and shape of the torque devices currently used in the art, which provides experienced operators with a familiar feel and function of the devices the operators have previously used. The neck portion 220 preferably has a smaller diameter than the nose portion 210 and the base portion 230 so as to provide maximal capability to rotate the guidewire 100. In addition, the shape of the hexagonal outer perimeter 237 of the neck portion 220 provides a distinct tactile advantage over the smooth uniform cylindrical surface of the torque devices currently used in the art. Finally, the base portion 230 is shaped for improved balance and feel and the varied diameter of the preferred embodiment allows fine continuous variable control of the guide wire 100 depending on finger position along the tear drop shaped axis. As may be understood by one of the art, the neck portion 220 may have a variety of different shapes, including a circular or polygonal cross-section.

Figure 6A:
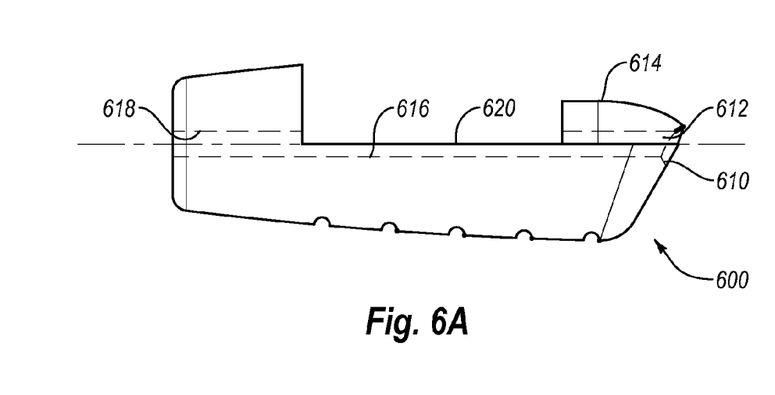
FIG. 6A is a side view of a bottom component of a base segment of a torque device according to another embodiment of the invention.

FIGS. 6A-10 illustrate a means for fixing the guidewire 100 within a torque device 1000 according to a modified embodiment of the invention. FIGS. 6A-6B illustrate an embodiment of a base bottom piece 600 and FIGS. 7A-7B illustrate a corresponding base top piece 700. Together the base bottom piece 600 and the base top piece 700 form an alternate embodiment of a base portion 230 which may be used in association with the nose portion 210 and the neck portion 220 described in FIGS. 2-5. FIGS. 8A-8B show the base bottom piece 600 and the base top piece 700 assembled together, with the assembled base portion 750 being in closed position so as to lock and secure the guidewire 100. FIGS. 9A-9B show the base bottom piece 600 and the base top piece 700 assembled together, with the assembled base portion 750 being in open position so that the guidewire 100 is able to traverse through the bore of the torque device 1000 without being restricted by the torque device 1000.

Figure 6B:
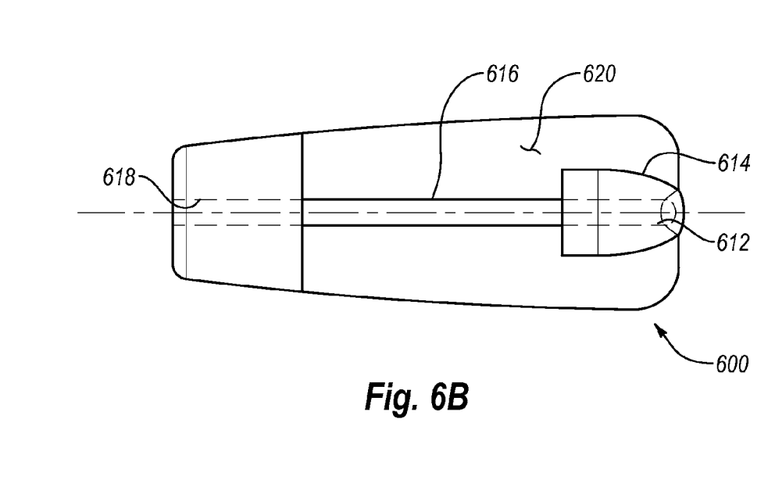
FIG. 6B is a top view of the bottom component of the base segment of FIG. 6A.

The base bottom piece 600 shown in FIGS. 6A-6B has a modified teardrop shape with a cut away segment which corresponds with the shape of the base top piece 700. The base bottom piece has approximately a 1 inch length, with a front or proximal diameter of ¼ inch and a distal or rear diameter of approximately ⅜ inches. In a preferred embodiment, the cut away portion which conforms to the shape of the base top piece 700 begins ¼ inches from the proximal end and extends as a flat surface 620 toward the distal end of the base bottom piece 600. A bore 618 is formed through the center or middle of the base bottom piece 600 and a wire locking groove 616 is formed at the midportion of the base bottom piece 600 which has a wider diameter than the bore 618. For example, while the bore 618 has a diameter of 0.040 inches, the wire locking groove 616 has a diameter of 0.050 inches and extends ½ inch from the proximal end of the base bottom piece 600. In the area of the wire locking groove 616, the guidewire 100 is exposed from within the housing of the base bottom piece 600 when the guidewire 100 is housed within so as to be available for contact with a wire-locking ridge 712 of the base top piece 700 as is described more fully below.

At the distal portion of the base bottom piece 600 a guidewire housing portion 614, which has an inverted U-shape, a length of 3/16 to ¼ inch long which projects approximately 1/16 inch off the flat surface 620 with a bore 612 formed therein. In a preferred embodiment, the bore 612 has a diameter of approximately 0.050 inches and may include a tapered opening 610.

Figure 7A:
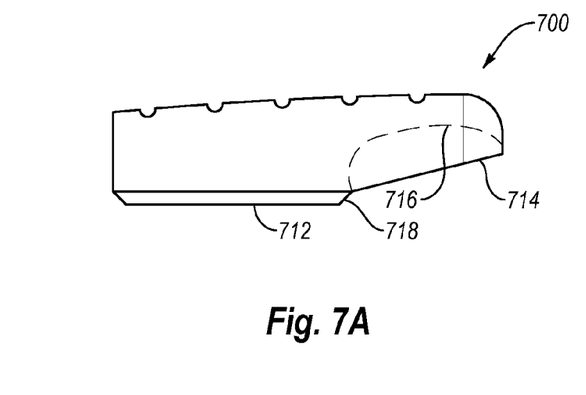
FIG. 7A is a side view of a top component of a base segment of a torque device which corresponds to the bottom component of FIG. 6A.
Figure 7B:
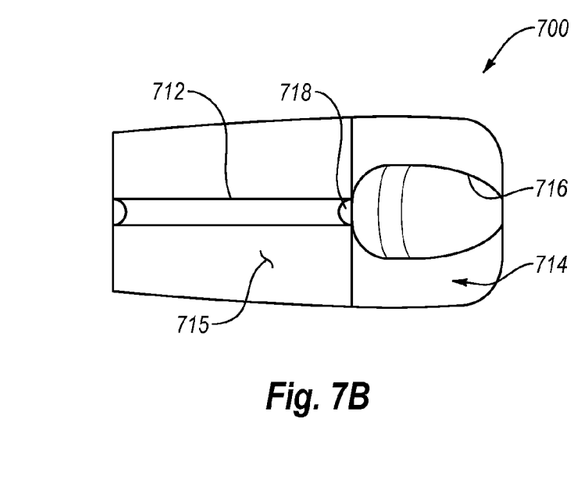
FIG. 7B is a top view of the top component of the base segment of FIG. 7A.

FIGS. 7A-7B illustrate a base top piece 700 which corresponds to the base bottom piece 600. In a preferred embodiment, the base top piece 700 has a length of ¾ inch, a proximal diameter of 5/16 inch and a distal diameter of 7/16 inch. The shape of the base top piece 700 has a shape so as to correspond to the shape of the base bottom piece 600. A flat surface 715 is 7/16 to 1/2 inch long and is designed to sit flush with the flat surface 620 of the base bottom piece 600.

A wire locking ridge 712 formed in a bottom surface of the base top piece 700 is designed to fit into the wire-locking groove 616 of the base bottom piece 600. A curved surface 714 is 1/4 to 5/16 inch long and has a predetermined angle to allow a rocking motion when an operator applies pressure to the distal portion of the base top piece 700 with respect to a base bottom piece 600. The predetermined angle is preferably between 12 and 14 degrees and allows clearance of the wire locking ridge 712 from locking in the wire locking groove 616 when the base top piece 700 is rocked or pivoted with respect to the base bottom piece 600.

The wire-locking ridge 712 is preferably 7/16 inch long and fits within the wire-locking groove 616 with sufficient tolerance to ensure that the guidewire 100 is securely held while in the locked position without crimping or damaging the guidewire 100. In a preferred embodiment, the forward and back edges of the wire locking ridge 712 could be beveled 718 to facilitate smooth wire entry and sliding through the base portion 750. In one configuration, the forward edge bevel (not shown) may be more pronounced than the back bevel 718. The base top piece 700 may also include a cavity or recess 716 to accommodate the wire locking groove 616 of the base bottom piece 600.

Figure 8A:
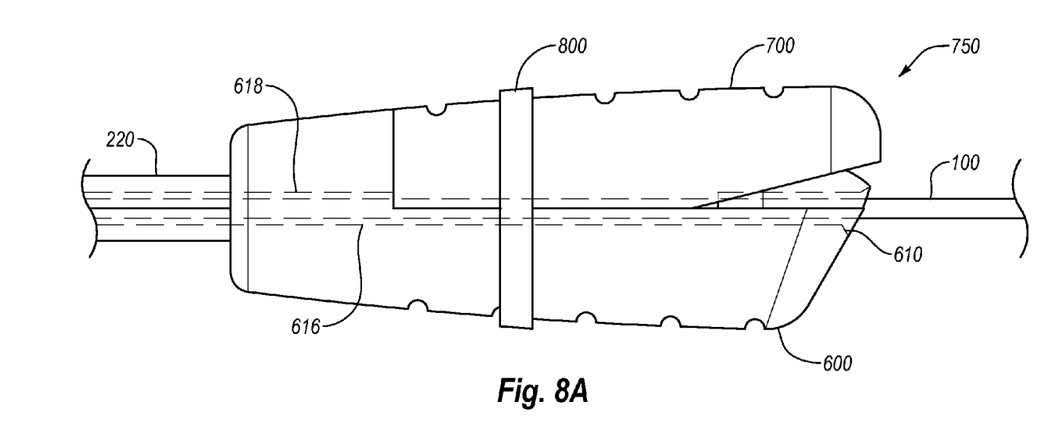
FIG. 8A is a side view of the base segment assembly including both the top and bottom components, where the base segment is in closed position.
Figure 8B:
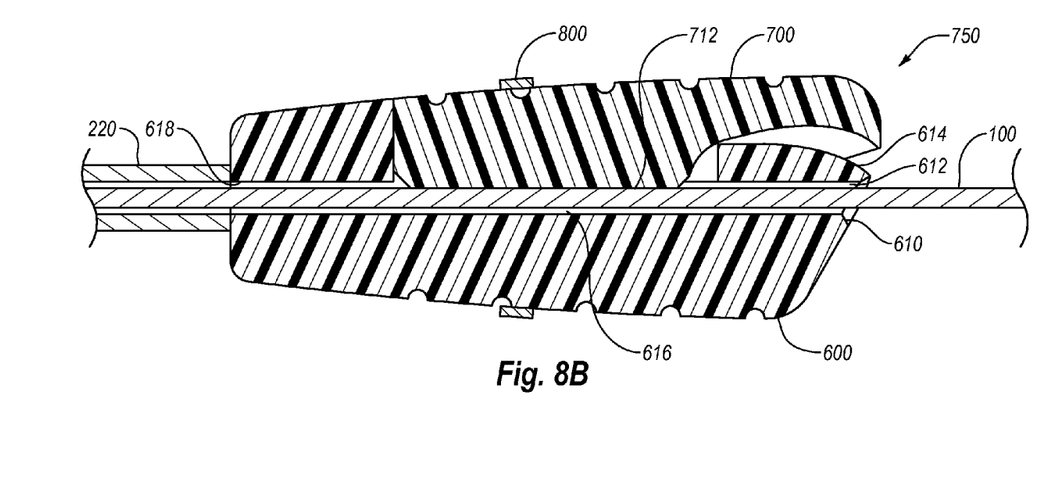
FIG. 8B is a cross-portion of the side view of the base segment assembly of FIG. 8A.
Figure 9A:
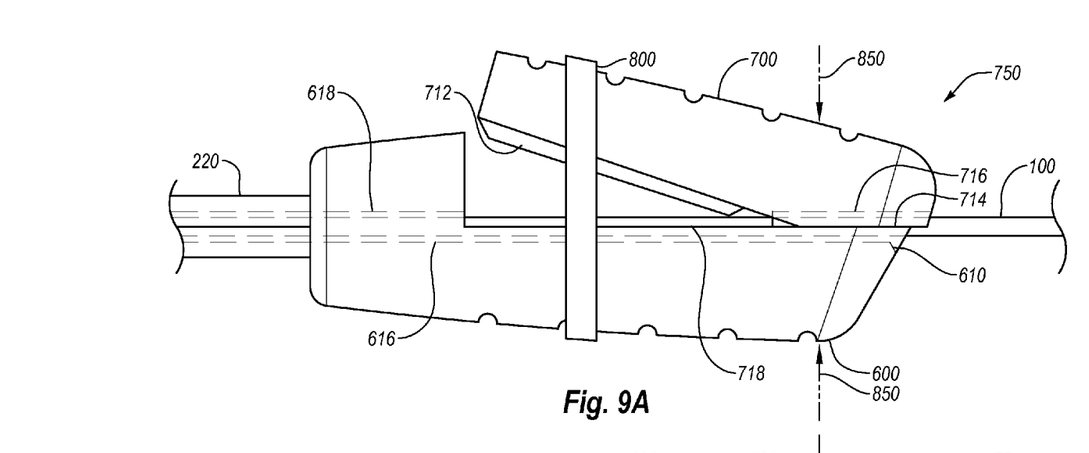
FIG. 9A is a side view of the base segment assembly including both the top and bottom components, where the base segment is in open position.
Figure 9B:
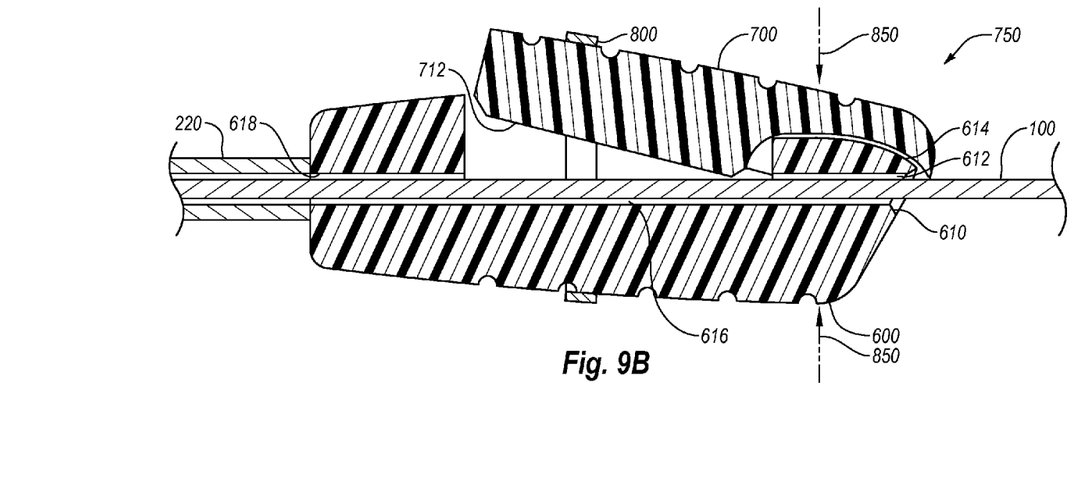
FIG. 9B is a cross-portion of the side view of the base segment assembly of FIG. 9A.

FIGS. 8A-8B show the base top piece 700 and base bottom piece 600 assembled together in an assembled base portion 750. In the configuration shown in FIGS. 8A-8B the assembled base portion 750 is in closed position on the guidewire 100. The base bottom piece 600 shown in FIGS. 8A-8B is held together with the base top piece 700 by a retention band 800, which provides the force to keep the base bottom piece 600 and the base top piece 700 in closed position.

As shown in FIGS. 8A-8B, the force applied by the retention band 800 causes the wire-locking ridge 712 of the base top piece 700 to pinch or compress the guidewire 100 against the wire-locking groove 616 of the base bottom piece 600, locking the guidewire 100 in place. Using this configuration, the default position of the assembled base portion 750 is in the closed or locked position As the operator pinches or compresses the distal portion of the assembled base portion 750 with a force 850, the force 850 overcomes the force applied by the retention band 800 which causes the base top piece 700 to move from the locked position with respect to the base bottom piece 600. As such. the compression force 850 causes the top base piece 700 to rock or pivot with respect to the base bottom piece 600, causing the wire-locking ridge 712 to correspondingly pivot upwards and away from the wire locking groove 616, releasing the pressure or locking tension applied to the guidewire 100 and allowing the guidewire 100 to pass through the bore 618 and guidewire housing portion 614 without restraint.

In an alternative configuration, the force to hold the base top piece 700 and the base bottom piece 600 in locked position would be provided by a spring, a pin, a clamp, a U-shaped piece or the like.

In one preferred embodiment, a hinge may be provided in the base top piece 700 and the base bottom piece 600 so as to act as a fulcrum to hold the base top piece 700 and the base bottom piece 600 together if a spring or other pushing force is used. Such a hinge would also provide a pivoting point allowing the base top piece 700 to pivot with respect to the base bottom piece 600.

Figure 10:
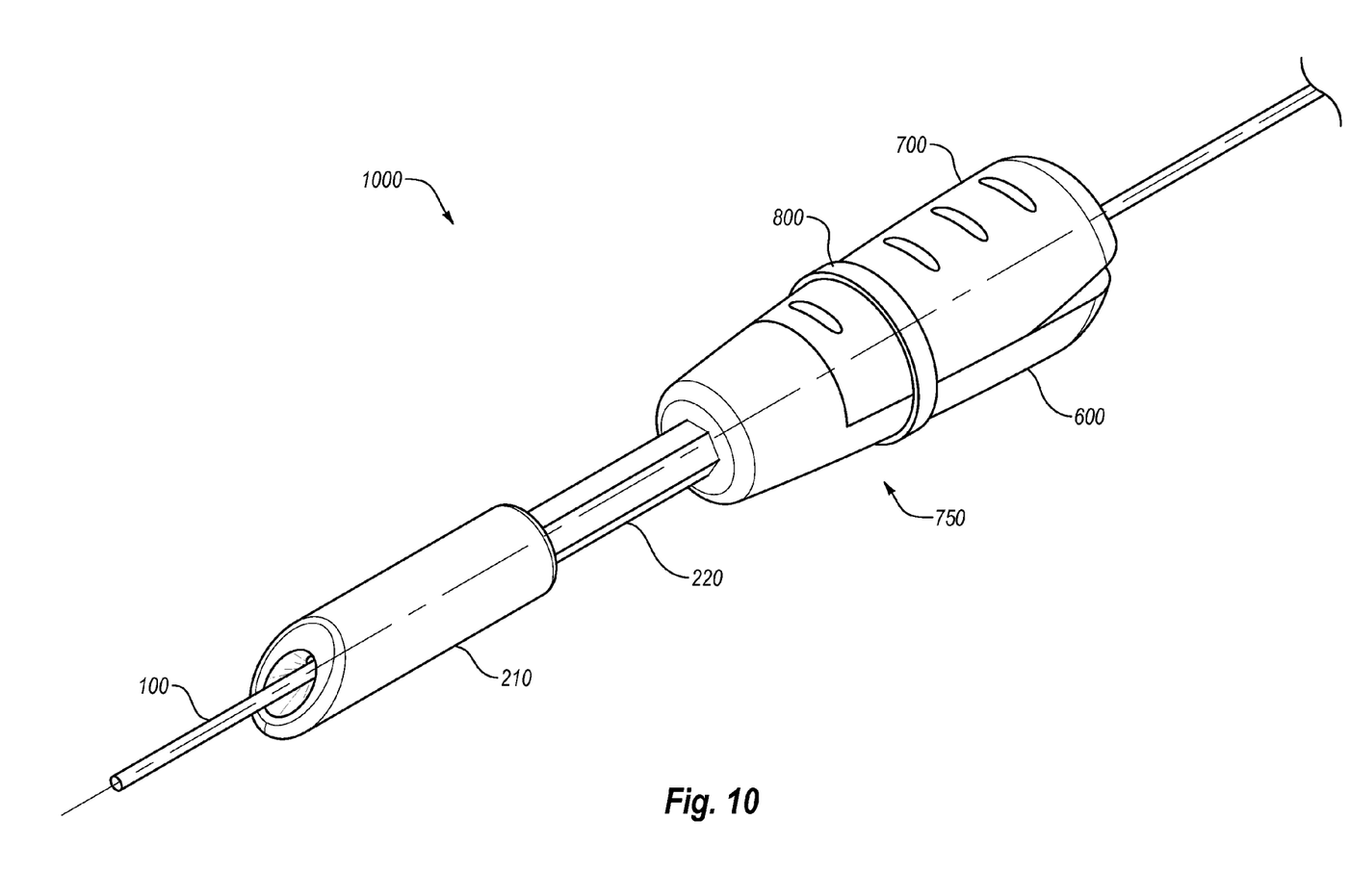
FIG. 10 is an isometric view of the torque device according to the embodiment shown in FIGS. 6A-9B, the base segment assembly being in closed position.

FIG. 10 is an isometric view of the torque device 1000 with an assembled base portion 750. The configuration offers various benefits, including a locking and repositioning mechanism that can be performed with one hand, rather than the two-handed fixing mechanisms currently taught by the art. Specifically, as needed during the procedure, the operator can use the same hand used to manipulate the rotation and translation of the torque device 1000 to compress the proximal end of the assembled base portion 750, causing the force applied by the retention band 800 to be overcome such that the guidewire 100 is released from the locked position. Then, the operator may slide the torque device 1000 to the desired location on the guidewire 100 and re-secure the guidewire 100 by releasing the proximal end of the assembled base portion 750 so that force applied by the retention band 800 causes the base top portion 700 to compress or pinch the guidewire 100 against the base bottom piece 600.

The embodiment described above provides vast benefits in the locking/unlocking, repositioning, translation or longitudinal manipulation of the torque device 1000 with respect to the guidewire 100 so as to provide the desired advancement or refraction of the guidewire 100 and corresponding wire tip. Finally, the removal of the torque device 1000 is also able to be simply removed from the guidewire 100 with only a single-handed operation. This frees an operator's hand for the insertion of an angioplasty balloon or stent on the guidewire 100.

The locking mechanism described above also reversibly clamps the torque device 1000 to the guidewire 100 without damaging the guidewire 100. Simultaneously, the locked position provides a one-to-one application of a torque force from the torque device 1000 to the tip of the guidewire 100 without the guidewire 100 slipping.

These benefits extend to increased procedural success since the torque device provides improved control and operation of the guidewire. There is also a decrease in the amount of time required to perform a procedure, which correspondingly reduces the amount of time a patient is subject to fluoroscopy, decreased patient and staff exposure to radiation, reduced rates of procedural complications, reduced patient sedation time, reduced procedural costs, and increased room throughput.

As may be understood by one of skill in the art, the embodiments herein may be performed in a variety of different configurations without departing from the meaning or scope of the invention and while ensuring some of the benefits described herein. For example, a variety of differing sizes and shapes may be used and any number of materials may be used to form the torque device. Further, although the embodiments described herein describe both a single molded torque device where the nose, neck and base portion are all formed together in a single process and an interchangeable configuration where each of the nose, neck and base portion are separately formed and then subsequently assembled, any variety of assemblies may be used.

For example, in another configuration, the torque device may be comprised of two pieces, preferably formed of plastic, where the nose portion 210, neck portion 220, and the base bottom piece 600 are formed together and comprise a single piece of molded plastic, while the base top piece 700 forms a separate piece of molded or otherwise manufactured plastic which is subsequently attached to the single piece of molded plastic using one of the means described above.

Further, although the embodiments described above describe the use of each of a nose portion 210, a neck portion 220, and either a base portion 230 or an assembled base portion 750, the invention may use a subset of these components. For example, the assembled base portion 750 may be utilized as a stand-alone torque device. Additionally, the assembled base portion 750 may also be used with only the neck portion 220 or only the nose portion 210.

Figure 11:
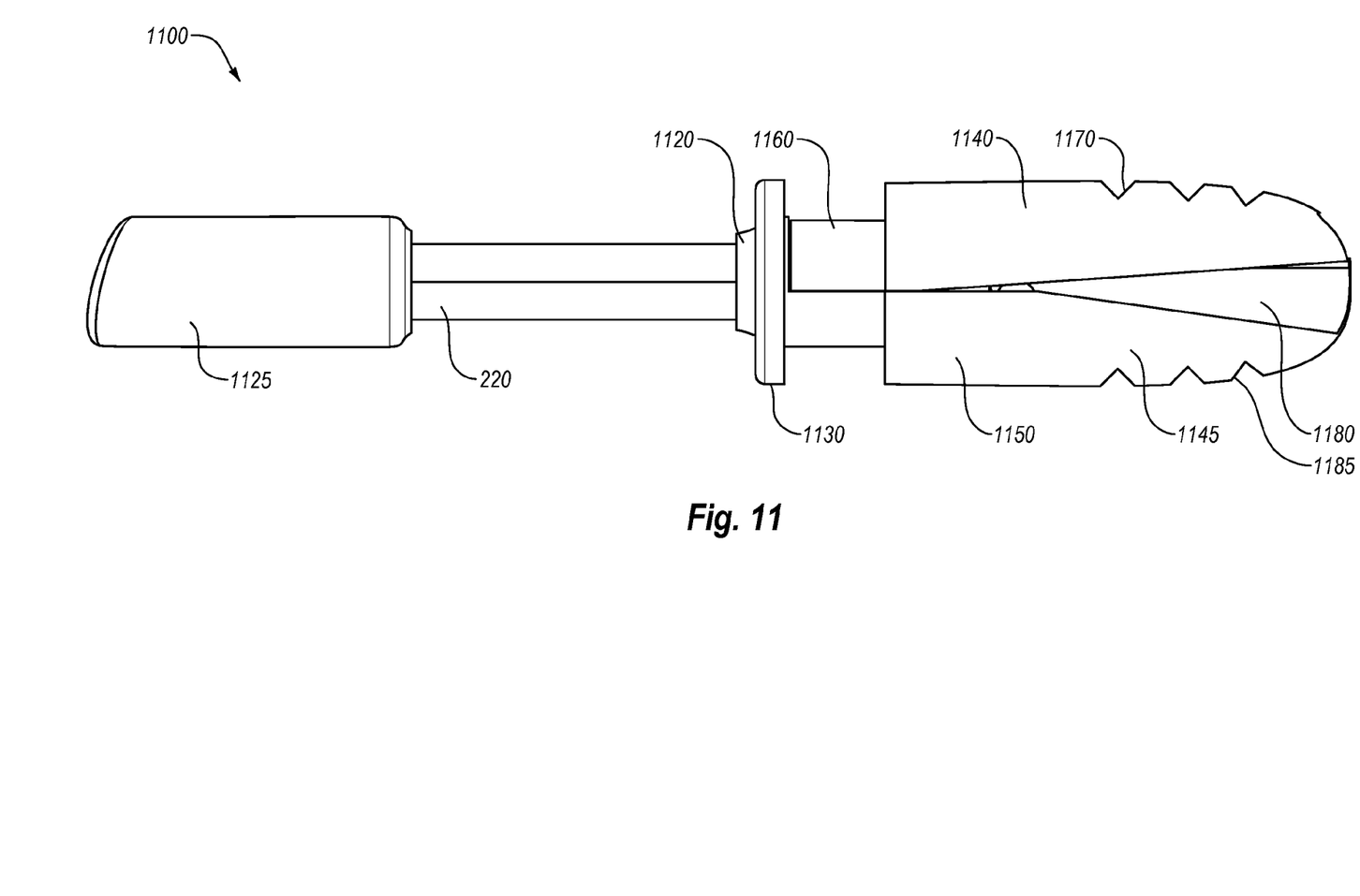
FIG. 11 is a side view of a torque device according to a third embodiment of the invention.
Figure 17:
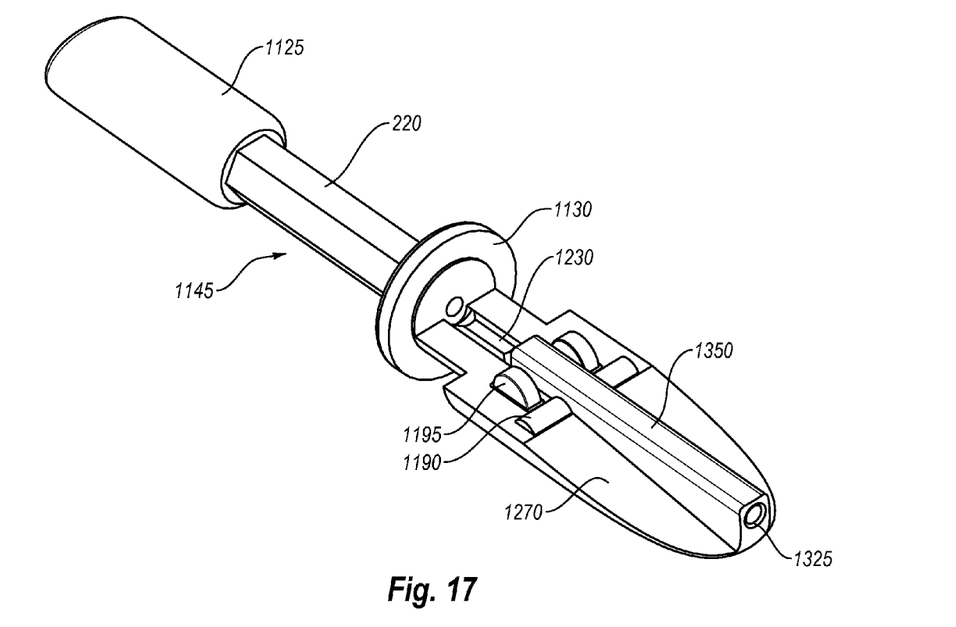
FIG. 17 is an isometric view of the bottom component of the base segment assembly according to the third embodiment, which is incorporated with the nose and neck portions.
Figure 18:
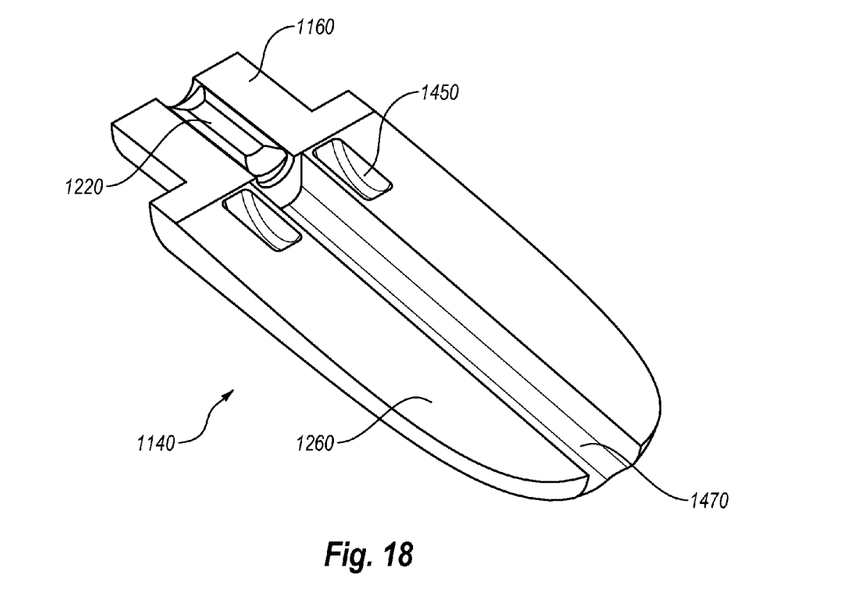
FIG. 18 is an isometric view of the top component of the base segment assembly according to the third embodiment.

FIGS. 11-18 illustrate a third embodiment which may implement aspects of the invention. FIG. 11 is a side view of the additional example of a torque device 1100 which is capable of performing various aspects of the invention. As with the previous embodiments, the torque device 1100 includes three main segments, including a nose portion 1125, a neck portion 220, and an assembled base portion 1150 which includes a base bottom portion 1145 and a base top portion 1140. As is shown in FIG. 17, the nose portion 1125, neck portion 220, and the base bottom portion 1145 may be integrated together as a single component which operate together with the base top portion 1140 shown in FIG. 18.

Returning to FIGS. 11 and 12, the torque device 1100 includes a collar portion including a first collar portion 1120 and second collar portion 1130. The base bottom portion 1145 includes a narrowed portion 1165 which together with a narrowed portion 1160 form a cylinder through which the guide wire 100 passes. The base bottom portion 1145 also includes a ridge 1180 discussed more fully below.

Figure 12:
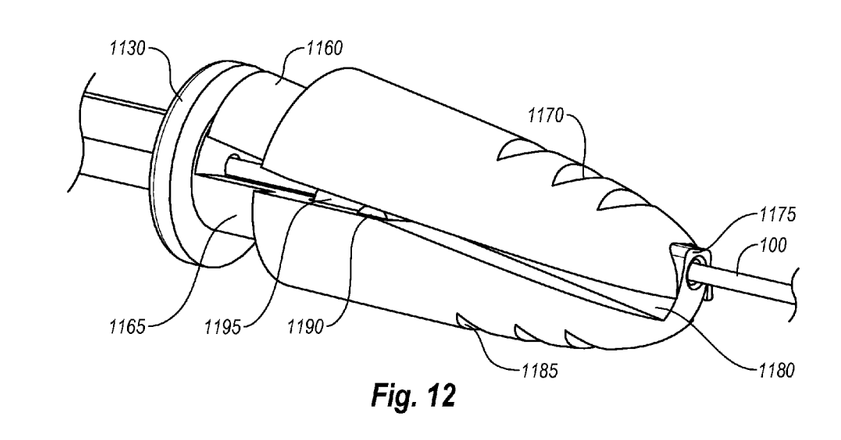
FIG. 12 is a side view of the base segment assembly including both the top and bottom components of the third embodiment of the invention.

In one embodiment, a retention band (not shown) may be placed on the outer circumference of the narrowed portion 1160 and 1165, the retention band may provide a compressive force which urges the base portion to be in the closed portion. Both the base bottom portion 1145 and the base top portion 1140 include contours and divots 1170 and 1185 for enabling grip.

As may be understood by one of skill in the art, one benefit of the first collar portion 1120 and second collar portion 1130 is that it stabilizes the placement of the base top portion 1140 and the retention band, if included.

As is shown in FIGS. 12 and 15-17, the base top portion 1140 includes a pair of recesses 1450 which have the shape of a half cylinder, which correspond to half-cylindrically shaped stabilizers 1195 formed on the base bottom portion 1145. The base bottom portion 1145 also includes a pair of fulcrum points 1190 on which the base top portion 1140 rocks as the torque device 1100 moves between open and closed positions. The stabilizers 1195 prevent lateral movement as the base top portion 1140 pivots on the base bottom portion 1145. The base top portion 1140 includes a groove 1470 formed along a flat surface 1260 which extends along a long axis which houses a long axis ridge 1350 formed along the angled surface 1270 which contains an inner bore 1325 which houses the guide wire 100. The groove 1470 and ridge 1350 also prevent lateral movement as the torque device 1100 moves between open and closed position.

Figure 13:
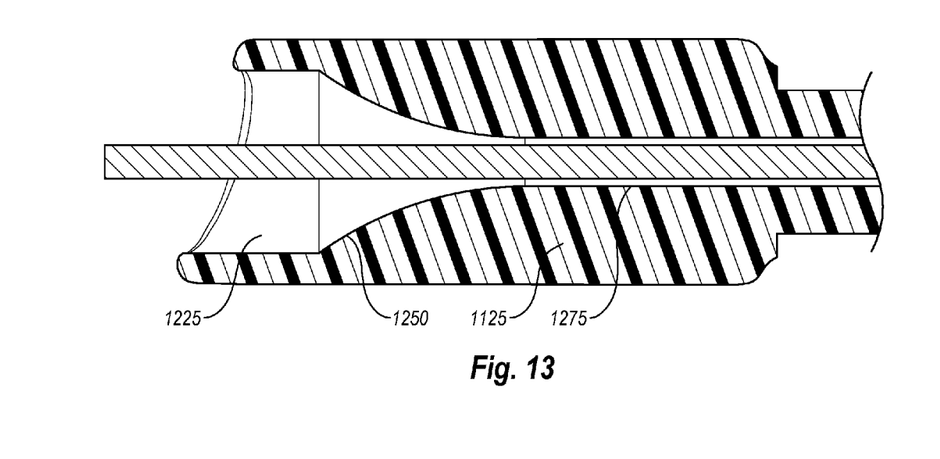
FIG. 13 is a side view of the nose portion of the third embodiment of the invention.

FIG. 13 illustrates a nose portion 1125 of the torque device 1100. Similar to the configurations described above, the nose portion 1125 includes a beveled front or distal end so as to facilitate loading of the guidewire 100 and so as to provide a visual guide with respect to the rotational orientation or position of the guidewire 100.

The bore 1275 of the nose portion 1125 also includes a conical front end recess 1225 which tapers at the section 1250 to meet the diameter of the bore 1275. In some embodiments, the nose portion 1125 may be rotated about the neck 220 so that the beveled portion is rotated with respect to the base top portion 1140 and the base bottom portion 1145.

Figure 14:
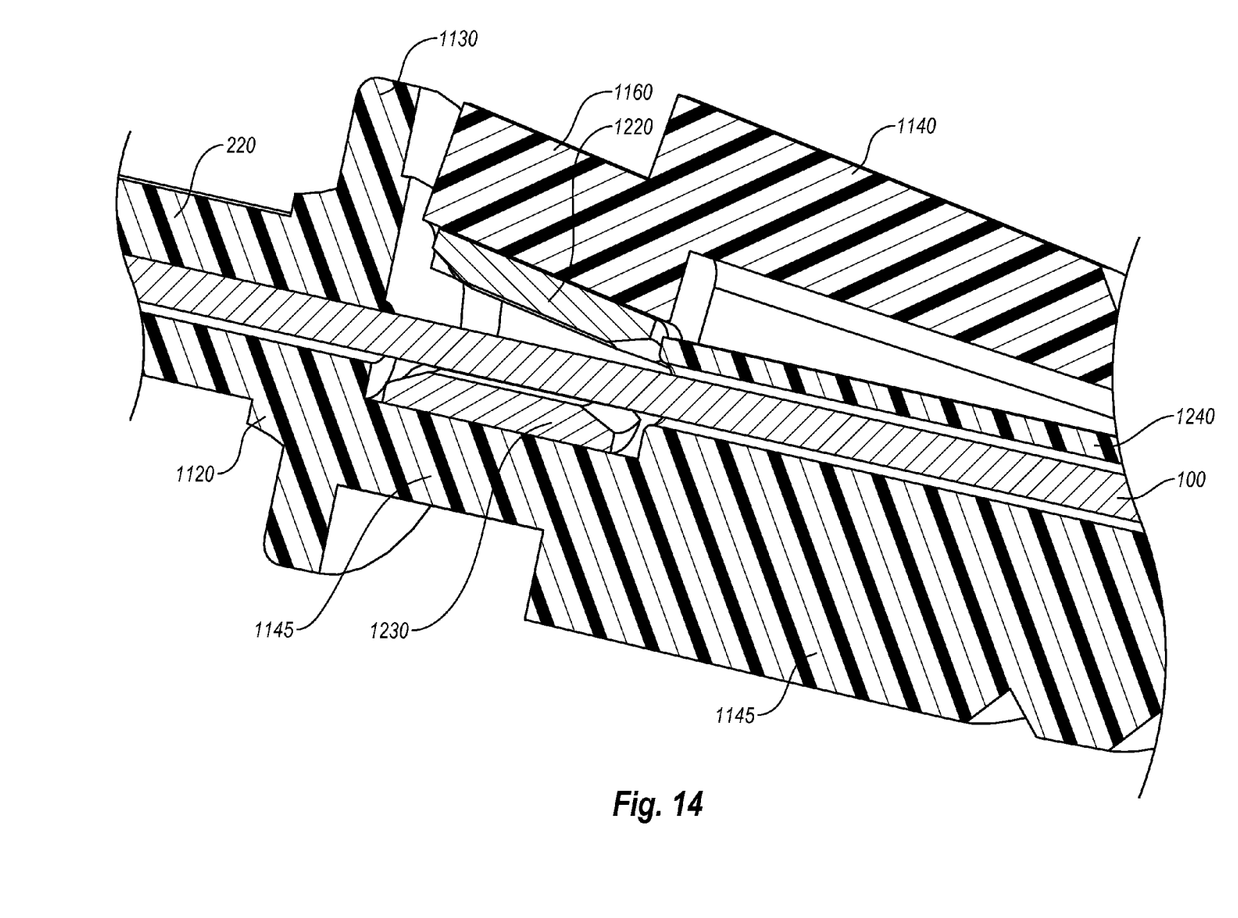
FIG. 14 is a cross-portion of the base segment assembly according to the third embodiment when the base segment assembly is in the open position.
Figure 15:
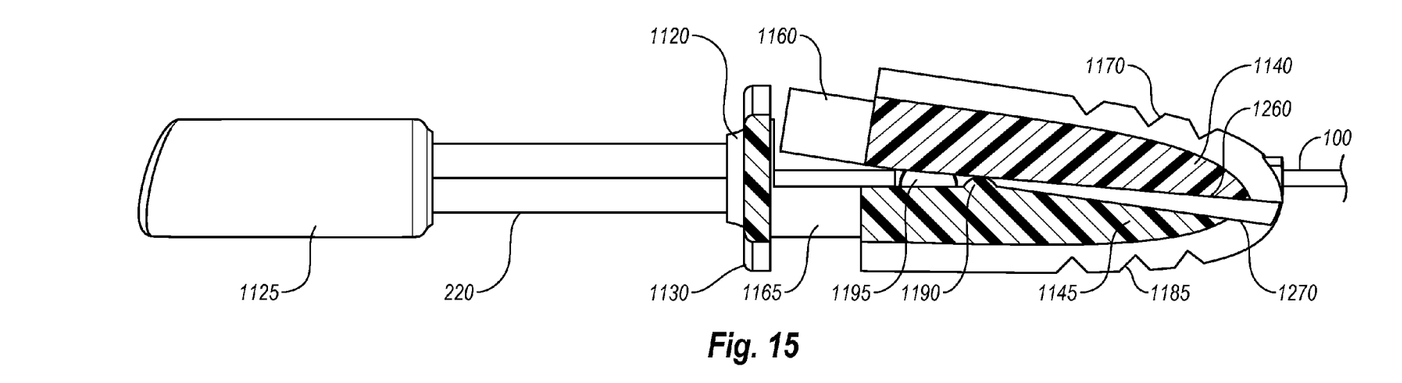
FIG. 15 is a side view of the torque device according to the third embodiment when the base segment assembly is in the open position.
Figure 16:
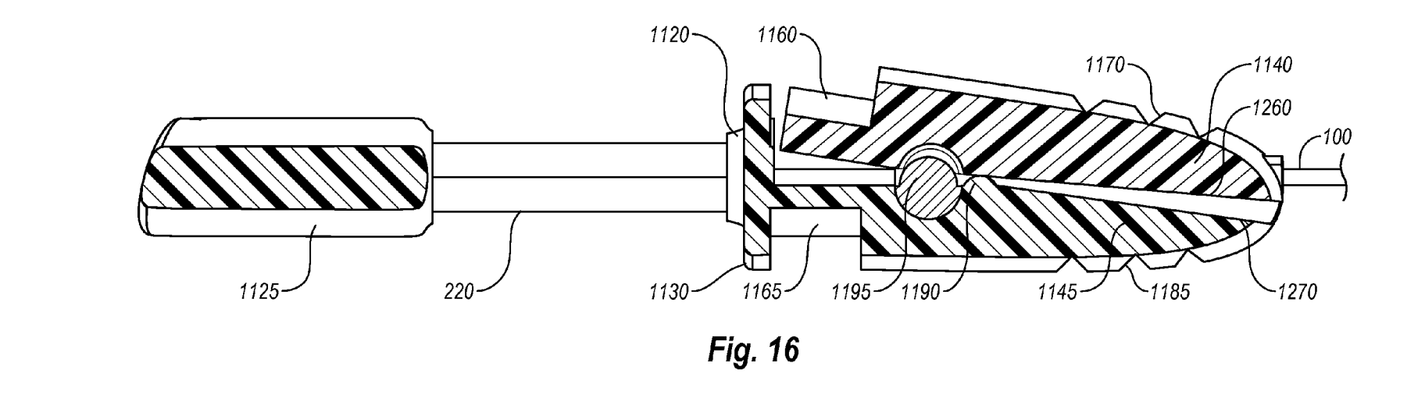
FIG. 16 is a side view of the torque device according to the third embodiment when the base segment assembly is in the open position with a partial cutaway which shows a fulcrum point of the base segment.

As is shown in FIG. 14, the base top portion 1140 and the base bottom portion 1145 both include contact segments 1220 and 1230, which may comprise a band blasted metal insert which optimize the capture and retention of the guide wire 100 when the torque device 1100 is in closed position. As may be understood by one of skill in the art, the contact segments may be omitted. Further, the contact segments 1220 and 1230 may be formed from a variety of materials. As is also shown in FIG. 14, the ridge 1350 includes a lumen 1325 which encloses the guidewire 100 with an upper surface 1240 being formed adjacent to the contact segment 1220. Further, the groove 1470 and ridge 1350 also prevent lateral movement as the torque device 1100 moves between open and closed position.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A medical torque device comprising:
a nose portion having a first outer circumference;
a neck portion having a second outer circumference, the second outer circumference being smaller than the first outer circumference; and
a base portion having a third outer circumference which is greater than the second outer circumference;
wherein a distal end of the neck portion is connected to a proximal end of the nose portion and the base portion with an inner lumen which extends through the nose portion, neck portion, and base portion and through which a guidewire passes,
wherein the second outer circumference has a continuous non-spherical shape such that the guidewire is completely enclosed and no portion of the guidewire is exposed within the neck portion.

2. The medical torque device of claim 1, wherein the nose portion includes a beveled distal end opposite to an end which is connected to the neck portion.

3. The medical torque device of claim 1, wherein the inner lumen at a beveled distal end of the nose portion includes a conical front end recess which has a larger diameter than the lumen at a region where the nose portion is connected to the neck portion.

4. The medical torque device of claim 1, wherein the second outer circumference has a polygonal shape having at least three sides and at least three vertices where the sides meet.

5. The medical torque device of claim 1, wherein the base portion comprises a base top portion and a base bottom portion, wherein an urging means is configured to urge the base top portion toward the base bottom portion and with the guidewire positioned therebetween, so as to hold the guidewire in place in a closed position.

6. The medical torque device of claim 5, wherein the base top portion and the base bottom portion are configured so that an operator is able to apply a counter force which causes the base top portion to be moved away from the base bottom portion so that the urging force applied to the guidewire is removed and to cause the base top portion and the base bottom portion to move from the closed position to the open position.

7. The medical torque device of claim 1, wherein the base portion has a conical outer circumference wherein a distal end of the base portion at a region where the base portion is connected to the neck portion has a smaller circumference than a proximal end of the base portion.

8. A medical torque device comprising:
a first component comprising:
a nose portion having a first outer circumference;
a neck portion having a second outer circumference, the second outer circumference being smaller than the first outer circumference;

a base bottom portion having a guidewire-locking groove where a guidewire positioned within the base bottom portion is exposed; and an inner lumen which extends through the nose portion, neck portion and base bottom portion which houses the guidewire;

a base top portion including a guidewire-locking ridge which is capable of applying a pinching force on the guidewire positioned within the guidewire-locking groove when the first component and the base bottom position are urged together; and an urging means configured to urge the base top portion towards the base bottom portion of the first component.

9. The medical torque device of claim 8, wherein the nose portion includes a beveled distal end opposite to an end which is connected to the neck portion.

10. The medical torque device of claim 8, wherein an inner lumen at the beveled distal end of the nose portion includes a conical front end recess which has a larger diameter than the lumen at a region where the nose portion is connected to the neck portion.

11. The medical torque device of claim 8, wherein the second outer circumference has a non-spherical shape.

12. The medical torque device of claim 11, wherein the second outer circumference has a polygonal shape having at least three sides and at least three vertices where the sides meet.

13. The medical torque device of claim 8, wherein the base top portion and the base bottom portion are configured so that an operator is able to apply a counter force which causes the base top portion to be moved away from the base bottom portion so that the urging force applied to the guidewire is removed and to cause the medical torque device to move from a closed position where the pinching force is applied to the guidewire to an open position where no pinching force is applied to the guidewire.

14. The medical torque device of claim 8, wherein the base top portion and the base bottom portion together form an assembled base portion which has a conical outer circumference wherein a distal end of an assembled base top portion and first portion at a region where the base bottom portion connected to the neck portion has a smaller circumference than a proximal end of the assembled base portion.

15. The medical torque device of claim 8, wherein one of base top portion and the base bottom portion includes a hinge which enables the base top portion to pivot with respect to the first component.

16. A medical torque device comprising:
a first component comprising:
a nose portion having a cylindrical shape having a first outer circumference;
a neck portion having a cylindrical shape having an outer circumference with a cross-section with a polygonal shape having at least three sides and at least three vertices where the sides meet;
a base bottom portion having a guidewire-locking groove where a guidewire positioned within the base bottom portion is exposed; and
an inner lumen which extends through the nose portion, neck portion and base bottom portion which houses the guidewire;
a base top portion including a guidewire-locking ridge which is capable of applying a pinching force on the guidewire positioned within the guidewire-locking groove when the first component and the base bottom position are urged together; and
an urging means configured to urge the base top portion towards the base bottom portion of the first component,
wherein the base top portion and the base bottom portion together form an assembled base portion which has a conical outer circumference wherein a distal end of an assembled base top portion and first portion at a region where the base bottom portion connects to the neck portion has a smaller circumference than a proximal end of the assembled base portion.

17. The medical torque device of claim 16, wherein the nose portion includes a beveled distal end opposite to an end which is connected to the neck portion.

18. The medical torque device of claim 16, wherein an inner lumen at the beveled distal end of the nose portion includes a conical front end recess which has a larger diameter than the lumen at a region where the nose portion is connected to the neck portion.

19. The medical torque device of claim 16, wherein the base top portion and the base bottom portion are configured so that an operator is able to apply a counter force which causes the base top portion to be moved away from the base bottom portion so that the urging force applied to the guidewire is removed and to cause the medical torque device to move from a closed position where the pinching force is applied to the guidewire to an open position where no pinching force is applied to the guidewire.

\* \* \* \* \*